(12) United States Patent  
Aizenberg et al.

(10) Patent No.: US 9,492,578 B2  
(45) Date of Patent: Nov. 15, 2016

(54) RECONFIGURABLE SURFACES FOR INFORMATION SECURITY AND PROTECTION OF PHYSICAL BIOMETRICS

(71) Applicant: President and Fellows of Harvard College, Cambridge, MA (US)

(72) Inventors: Joanna Aizenberg, Boston, MA (US); Tak Sing Wong, Allston, MA (US); Michael Bucaro, Hoboken, NJ (US)

(73) Assignee: President and Fellows of Harvard College, Cambridge, MA (US)

( * ) Notice: Subject to any disclaimer, the term of this patent is extended or adjusted under 35 U.S.C. 154(b) by 28 days.

(21) Appl. No.: 14/400,218

(22) PCT Filed: May 9, 2013

(86) PCT No.: PCT/US2013/040294  
§ 371 (c)(1),  
(2) Date: Nov. 10, 2014

(87) PCT Pub. No.: WO2013/169994  
PCT Pub. Date: Nov. 14, 2013

(65) Prior Publication Data  
US 2015/0124265 A1    May 7, 2015

Related U.S. Application Data

(60) Provisional application No. 61/646,012, filed on May 11, 2012.

(51) Int. Cl.  
| G06K 9/74 | (2006.01) |
| A61L 2/18 | (2006.01) |
| A61B 5/117 | (2016.01) |
| G06K 9/00 | (2006.01) |
| C11D 7/26 | (2006.01) |
| C11D 11/00 | (2006.01) |
| G01B 11/24 | (2006.01) |

(52) U.S. Cl.  
CPC ............... *A61L 2/18* (2013.01); *A61B 5/1172* (2013.01); *C11D 7/261* (2013.01); *C11D 11/0035* (2013.01); *C11D 11/0047* (2013.01); *G01B 11/24* (2013.01); *G06K 9/00013* (2013.01)

(58) Field of Classification Search  
CPC ........................................................ G06K 9/74  
USPC ............................................................ 356/71  
See application file for complete search history.

(56) References Cited

U.S. PATENT DOCUMENTS

| 7,323,033 B2 * | 1/2008 | Kroupenkine ......... B01D 69/06 210/490 |
| 8,683,642 B2 * | 4/2014 | Weng ...................... B08B 1/00 15/118 |
| 2012/0006911 A1 * | 1/2012 | Weng ...................... B08B 1/00 239/289 |

FOREIGN PATENT DOCUMENTS

| EP | 0957445 A2 | 11/1999 |
| WO | WO-2012012441 A1 | 1/2012 |
| WO | WO-2012/100099 A2 | 7/2012 |

OTHER PUBLICATIONS

Julian et al., "Virus transfer between fingerpads and fomites," Journal of Applied Microbiology, vol. 109, pp. 1868-1874, 2010.  
International Search Report and Written Opinion mailed on Nov. 4, 2013, in International Application PCT/US2013/040294, filed May 9, 2013, 9 pages.

* cited by examiner

*Primary Examiner* — Roy M Punnoose  
(74) *Attorney, Agent, or Firm* — Wilmer Cutler Pickering Hale and Dorr LLP

(57) ABSTRACT

Surfaces for information security and protection of physical biometrics, such as a fingerprint, is described. Such biometric information recording surface includes a plurality of raised structures that can reproduce a biometric information when a body part containing the biometric information is applied to the biometric metric information recording surface. The reproduced biometric information can be completely removed by applying a liquid to the plurality of raised structures without need to apply an external physical contact.

29 Claims, 6 Drawing Sheets

| Elevated View (Schematics) | Top View (Time-lapse) |

1. Initial Stage

2. Liquid Wicking

Volatile Liquid

3. Liquid Drying

4. Structure Reconfigured

RECONFIGURABLE SURFACES FOR INFORMATION SECURITY AND PROTECTION OF PHYSICAL BIOMETRICS

CROSS-REFERENCE TO RELATED APPLICATIONS

This application is a National Stage Entry of PCT International Application No. PCT/US2013/40294 filed on May 9, 2013 which claims the benefit of the earlier filing date of U.S. Provisional Patent Application No. 61/646,012, entitled "Reconfigurable Surfaces for Information Security and Protection of Physical Biometrics," filed on May 11, 2012, the content of which are incorporated in their entirety.

All patents, patent applications and publications cited herein are hereby incorporated by reference in their entirety in order to more fully describe the state of the art as known to those skilled therein as of the date of the invention described herein.

COPYRIGHT NOTICE

This patent disclosure may contain material that is subject to copyright protection. The copyright owner has no objection to the facsimile reproduction by anyone of the patent document or the patent disclosure as it appears in the Patent and Trademark Office patent file or records, but otherwise reserves any and all copyright rights.

FIELD OF THE INVENTION

The present invention relates to surfaces that are capable of reproducing and completely removing or disrupting physical biometric information. More particularly, the present invention relates to surface that are capable of reproducing and completely removing fingerprints.

BACKGROUND

Physical biometrics, the intrinsic physical features unique to individuals, serves as innate signatures for personal identification. Since physical biometrics is commonly tied to sensitive personal information within many national and international organizations, accurate analysis of such biometric information is important. Moreover, protection of physical biometrics against unauthorized usage is also very important. Among the various physical biometrics available for identification, the fingerprint is the most accessible and widely used. As a result, mechanisms to accurately obtain, read, as well as prevent the unauthorized retrieval of fingerprints from surfaces (i.e., anti-fingerprint surfaces) are important.

Fingerprint residues present significant biometric security and health issues. Residues imprinted by the contact of the finger on a surface consist mostly of sebum (e.g., oils or lipids), sweat (i.e., salty water), and often infectious agents such as microbes and viruses which are retained on most smooth surfaces. Therefore, development of anti-fingerprint surfaces has focused on materials that exhibit reduced adhesion for both water and oil. The conventional approach for anti-fingerprint surfaces is to utilize materials with very low surface energy (i.e., the surface chemistry approach such that liquids have relatively low adhesion on these surfaces. Over the past decade, surface coatings/functionalization strategies have been successfully developed for metals, such as stainless steel, as well as optically transparent materials, such as glass and plastics. While these surfaces show improved anti-fingerprinting property, trace amounts of remnant residues can still be attached to even the lowest surface energy materials. A recent study has shown that disease pathogens can be transferred between human and fomites through the action of contact, which can act as an important route of transmission for both gastrointestinal and respiratory illness (Julian et al. *J. Appl. Microbiology* 109, 1868-1874, 2010). In high-traffic security areas (e.g., airport, government buildings, schools, offices, etc.) where fingerprinting is used for identification, such health-related issues become even more important. In order to address the security and health risks, external physical contacts, such as rubbing or wiping with a cloth, are currently employed. Manual cleaning is often impractical, too costly or presents additional security risks.

SUMMARY OF THE INVENTION

The invention described herein addresses the issues described above with the conventional techniques using automated renewal of the surface to erase biometric information and desanitize the surface.

In accordance with the present invention, a method of removing imprinted biometric information from surfaces is described.

In accordance with certain embodiments, the method includes providing a biometric information recording surface comprising a plurality of raised structures, reproducing a biometric information on the plurality of raised structures by applying a part of a body containing the biometric information to the biometric information recording surface, and removing the biometric information by applying a liquid to the plurality of raised structures without a need of applying an external physical contact.

In certain embodiments, the plurality of raised structures are clustered.

In certain embodiments, the plurality of raised structures include a polymer.

In certain embodiments, the plurality of raised structures include polydimethylsiloxane or polypropylene.

In certain embodiments, the biometric information is recorded after reproduction.

In certain embodiments, the liquid is a disinfecting liquid.

In certain embodiments, applying a liquid includes wicking the liquid between the plurality of raised structures to form unclustered plurality of raised structures.

In certain embodiments, removing the biometric information includes drying the liquid to form randomly clustered plurality of raised structures.

In certain embodiments, the biometric information recording surface is provided on an optical reader.

In certain embodiments, the optical reader is transparent.

In certain embodiments, the biometric information is a fingerprint.

In certain embodiments, the biometric information recording surface is a surface of a fingerprint reader in high-traffic security area, such as airport, government buildings, schools, offices and the like.

In certain embodiments, the biometric information recording surface is a surface of a personal number identification pad.

In certain embodiments, the biometric information recording surface is a surface of a safe.

In certain embodiments, the biometric information recording surface is a surface of a car door lock.

In certain embodiments, the biometric information recording surface is a surface of a touch screen device, such as smart phones, portable tablet computers, automated teller machines, televisions, and the like.

In accordance with the present invention, a biometric information identification device is described.

In accordance with certain embodiments, the device includes a biometric information reading optical reader, a biometric information recording surface comprising a plurality of raised structures that is capable of reproducing a biometric information on the plurality of raised structures, and a liquid that is capable of removing the biometric information by applying the liquid to the plurality of raised structures without a need of applying an external physical contact.

In certain embodiments, the plurality of raised structures are clustered.

In certain embodiments, the plurality of raised structures comprise a polymer.

In certain embodiments, the plurality of raised structures comprise polydimethylsiloxane or polypropylene.

In certain embodiments, the device further includes a storage device to record the biometric information after reproduction.

In certain embodiments, the liquid is a disinfecting liquid.

In certain embodiments, the optical reader is transparent.

In certain embodiments, the biometric information is a fingerprint.

In certain embodiments, the device is a fingerprint reader in high-traffic security area, such as airport, government buildings, schools, offices and the like.

In certain embodiments, the device includes a personal number identification pad.

In certain embodiments, the device is a safe.

In certain embodiments, the device includes a car door lock.

In certain embodiments, the device includes a touch screen device, such as a smart phone, a portable tablet computer, an automated teller machine, television, and the like.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIG. 1A-B shows surface having raised structures in an unclustered and clustered configurations in accordance with certain embodiments of the present invention;

FIG. 3 1-4 shows images illustrating how to completely remove the fingerprint nation reproduced on surfaces in accordance with certain embodiments of the present invention;

FIG. 4 shows the fine fingerprint details that was successfully captured by a commercially available optical fingerprint reader provided with the surfaces in accordance with certain embodiments of the present invention;

DETAILED DESCRIPTION OF THE INVENTION

In certain embodiments, a surface that is capable of reproducing biometric information, such as fingerprints, is described. In certain embodiments, surface is a multiuse surface capable of repeated use in the reproduction of fingerprints. In certain embodiments, the surface is further capable of removing reproduced biometric information. In certain embodiments, the surface can cleanly remove reproduced biometric information without the need to apply external physical contact, such as rubbing or wiping with a cloth. In certain embodiments, the surface is fully disinfected by the dispensed liquid.

In certain embodiments, the surface can be integrated into an optical reader apparatus (see, e.g., FIG. 6), The optical reader apparatus may include a surface in accordance with certain embodiments of the invention that is accessible to a finger. In certain embodiments, the surface may be provided over an optically clear substrate. In certain embodiments, the optical reader apparatus may be coupled with a computer interface for capturing an electronic image of the fingerprint. In certain embodiment, the optical reader apparatus may further contain a suitable liquid for removing the fingerprint. In certain embodiment, the optical reader apparatus may further contain a suitable liquid for disinfecting the surface.

Figure 1:
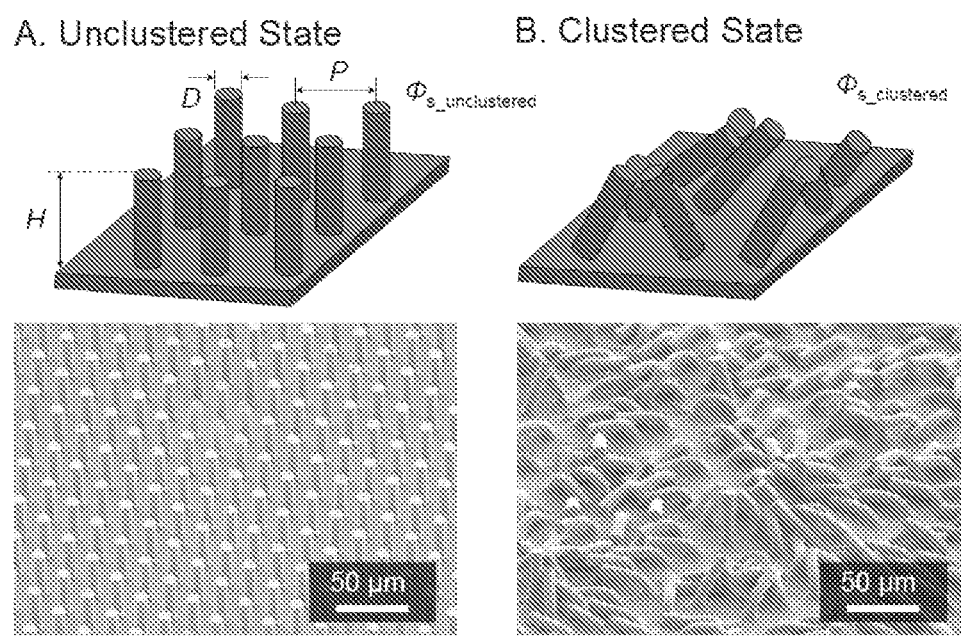

In certain embodiments, the surface includes a number of discrete structures in arbitrary geometries. The surface can include a number of discrete structures at a solid area fraction, $\Phi_s$. In certain embodiments, as shown in FIG. 1A, solid area fraction can be measured when the surface structures are free-standing and are unclustered, denoted as $\Phi_{s\_unclustered}$. In certain embodiments, as shown in FIG. 1B, solid area fraction can be measured when the surface structures are clustered together, denoted as $\Phi_{s\_clustered}$.

The structures can include an array of raised structures, such as posts that are cylindrical, rectangular, pyramidal, conical and the like. The characteristic sizes of the individual structures (i.e., height, diameter, and pitch of the structures, denoted as H, D, and P respectively) can be designed such that they are smaller than the distance between individual friction ridges of a fingerprint (i.e., on the order of 400 μm). Based on these geometrical parameters, $\Phi_{s\_unclustered}$ can be quantitatively expressed as $\pi(D/2)^2/P^2$.

The structures can be made using a variety of different materials, such as a polymer (e.g., thermally and/or radiation curable polymers, such as polydimethylsiloxane or polypropylene), ceramic, carbon fibers, and the like. The materials of the surface and the geometry of the structures can be tailored to produce a bending stiffness low enough to collapse under load while limited to deformations within their elastic limit, such that the surface returns to its original equilibrium position subsequently. For example, surfaces may employ materials with elastic moduli E, ranging from 1 MPa to 100 MPa depending on the geometry of the structures which may have dimensions ranging from 10 nm to 10 s of microns in radius, and length of submicrons to millimeters.

In certain embodiments, for applications where optical transparency is important (e.g., optical fingerprint reader), the clustered solid fraction, $\Phi_{s\_clustered}$ (i.e., when the surface structures are clustered), can be selected to maximize the light transmission through the surface. In particular, the upper limit of $\Phi_{s\_clustered}$ for cylindrical surface structures can be quantitatively estimated as $NDH/P^2$, where N is a constant related to the spatial arrangement of the surface structures (e.g., N=4 for square lattice arrangement).

In certain embodiments, these surface structures can be manufactured by any suitable methods, such as soil lithography techniques, replica molding, embossing, nanotube growth from the surface, fiber spinning, printing and the like. The formed surface structures may be unclustered as shown in FIG. 1A. Upon application of a suitable liquid and subsequent drying, the surface structures can be reconfigured to form a clustered structure as shown in FIG. 1B.

Figure 2:
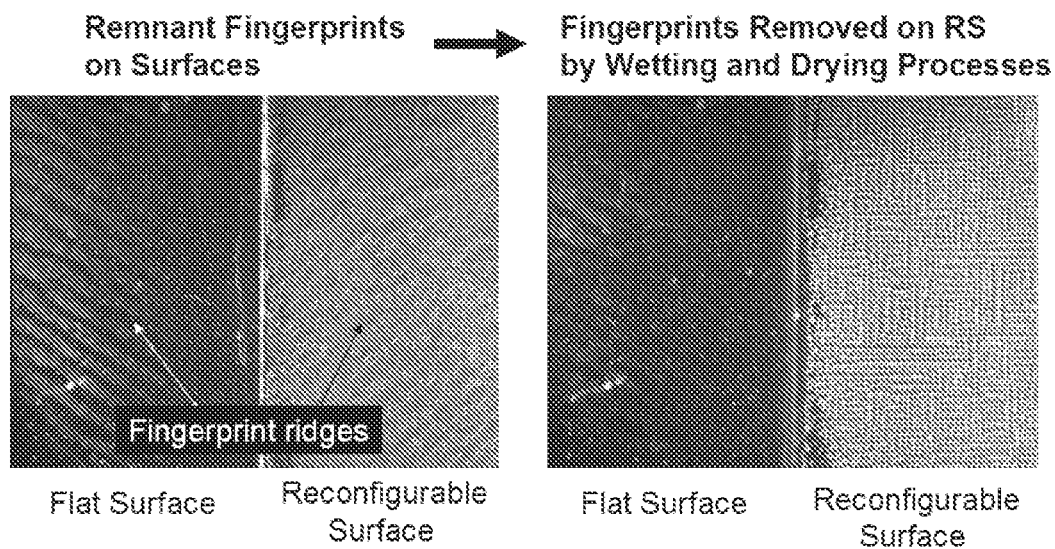
FIG. 2 shows surfaces that reproduce and remove fingerprints in accordance with certain embodiments of the present invention.

Upon application of a pressure with a finger, the fingerprint can be reproduced on the surface with high fidelity. FIG. 2, left, shows a comparison of the fingerprint formed on a flat surface as well as the surface in accordance with certain embodiments of the present invention. As shown, fingerprint is accurately reproduced on both the flat surface and the structured surface in accordance with certain embodiments of the present invention.

To remove the fingerprint, the surface can be rinsed with a suitable liquid, such as ethanol or isopropanol. Other suitable liquids include liquids that can remove sebum (e.g., lipids) and sweat (i.e., salty water) but that does not adversely affect the raised structures on surface. In addition, the liquids may further contain disinfecting properties, such as an antibacterial, germicidal, and the like properties. Suitable liquids include ethanol, hydrogen peroxide, isopropanol, acetone, and the like. As shown in FIG. 2, right, whereas the flat surface leaves behind the fingerprint residues after application of a droplet of ethanol, the surface in accordance with certain embodiments of the present invention leads to a completely randomized surface without any fingerprint pattern left.

Figure 3:
Figure 3:
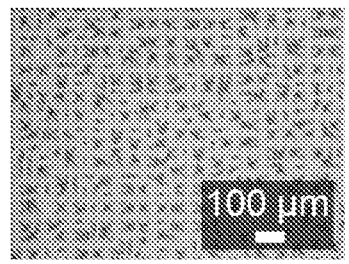
Figure 3:
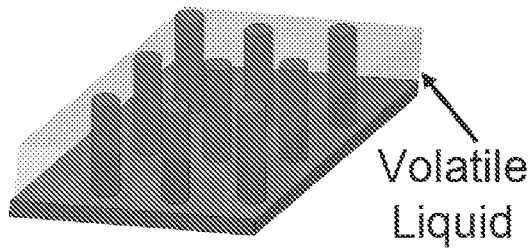
Figure 3:
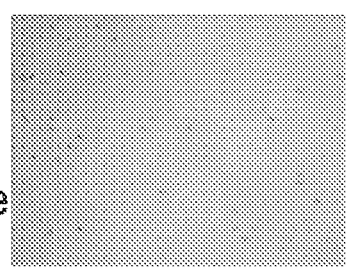
Figure 3:
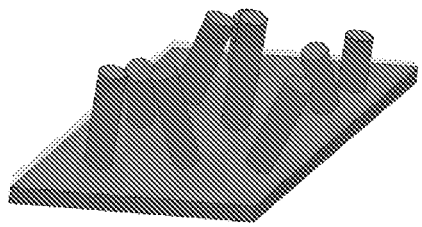
Figure 3:
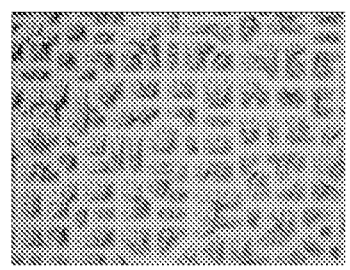
Figure 3:
Figure 3:
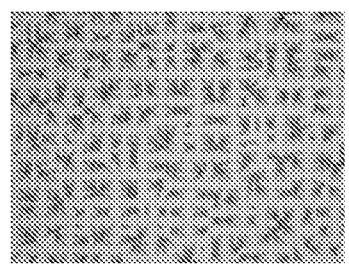

FIG. 3 shows how the surfaces in accordance with certain embodiments of the present invention are able to completely remove the fingerprint information reproduced thereon. As shown, the clustered structure having fingerprint reproduced thereon is provided with a liquid which is wicked into the structure. Wicking of the liquid leads to unclustering of the raised structures. As the liquid evaporates, the raised structures eventually cluster together randomly leading to a randomized clustered structure with erased fingerprint information. As a result, during the surface reconfiguration process, the effective solid area fraction, $\Phi_{s\_effective}$, of the surface falls within the range of $\Phi_{s\_unclustered} \leq \Phi_{s\_effective} \leq \Phi_{s\_clustered} \leq 1$.

Figure 4:
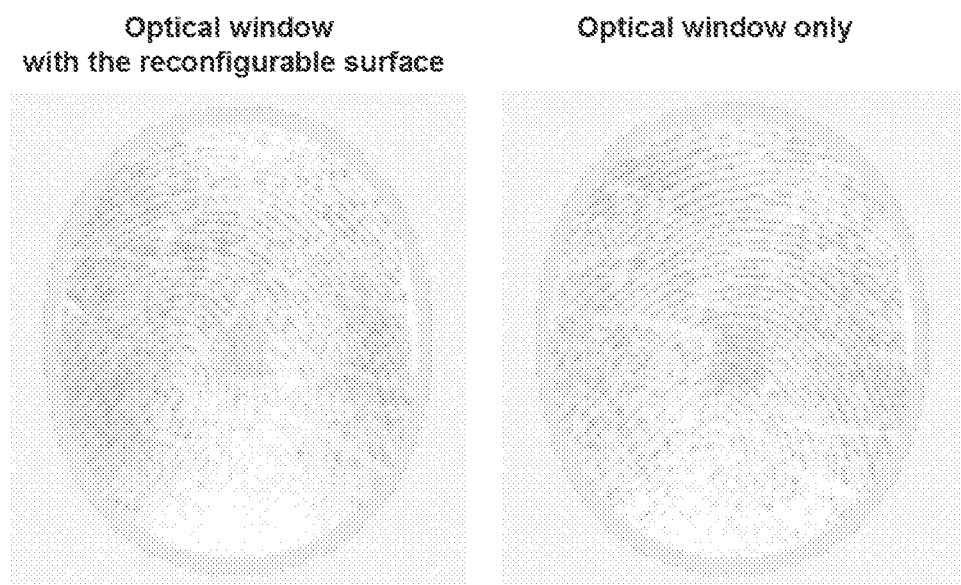

In certain embodiments, when $\Phi_{s\_effective}$ falls in the range between ~2.5% and ~50%, fine fingerprint details with high fidelity can be successfully captured by a commercially available optical fingerprint reader (see FIG. 4). This indicates that the presence of the surface topographies does not perturb the fingerprint recognition.

Without wishing to be bound by theory, the presence of the surface structures can serve at least two important functions. First, these structures can enhance the liquid wicking property, which can greatly increase the solid-liquid interface for residuals removal. Specifically, the Wenzel relationship states that the wettability enhances with the surface roughness, which can be quantitatively expressed as $\cos\theta^* = R\cos\theta$, where $\theta^*$, $\theta$, and R are the apparent contact angle of the textured surface, intrinsic contact angle of the material, and roughness factor of the surface, respectively. In addition, the roughness factor of the surface can be further expressed as $R = 1 + \pi DH/P^2$. By enhancing the roughness factor (i.e., R>>1), one can achieve a perfect wetting state with suitable liquids (i.e., $\theta^* = 0$ for $\theta < 90°$). Also, it is desirable to use liquids of low surface tension, $\gamma_{LV}$, due to their enhanced solid wettability.

Secondly, as shown in FIGS. 2 and 3, by selecting a material having a low bending stiffness, the structures may be able to reconfigure into randomized patterns through elastocapillary interactions during the liquid wetting and drying processes. Reconfiguration of the surface structures may stochastically randomize the residues left on surface. During the reconfiguration process, the surface structures may self-assemble into discrete domains of clustered regions, where the size of the cluster, N, is scaled as $\sim\gamma_{LV}H^3 \cos^2\theta/[D^2(P-D)^2E]$. Based on the scaling argument, the height, diameter, and the pitch of the surface structures are the important parameters to engineer the cluster size and morphology of the assembly. Different cluster combinations can also be achieved by appropriately adjusting the geometrical parameters, thereby increasing the reconfiguration capability of the surface.

The surface operates by stochastically reconfiguring deformable microscale and/or nanoscale surface structures through dynamic liquid wetting and drying processes, as well as disinfecting the contact surface. The biometric protection mechanism involves I) removal of residuals on the surface through a surface topography-induced liquid wicking process, and II) randomized reconfiguration of the residues left on individual structures through stochastic reorganization of the surface topographies during wetting and drying using a liquid disinfecting agent.

Figure 5:
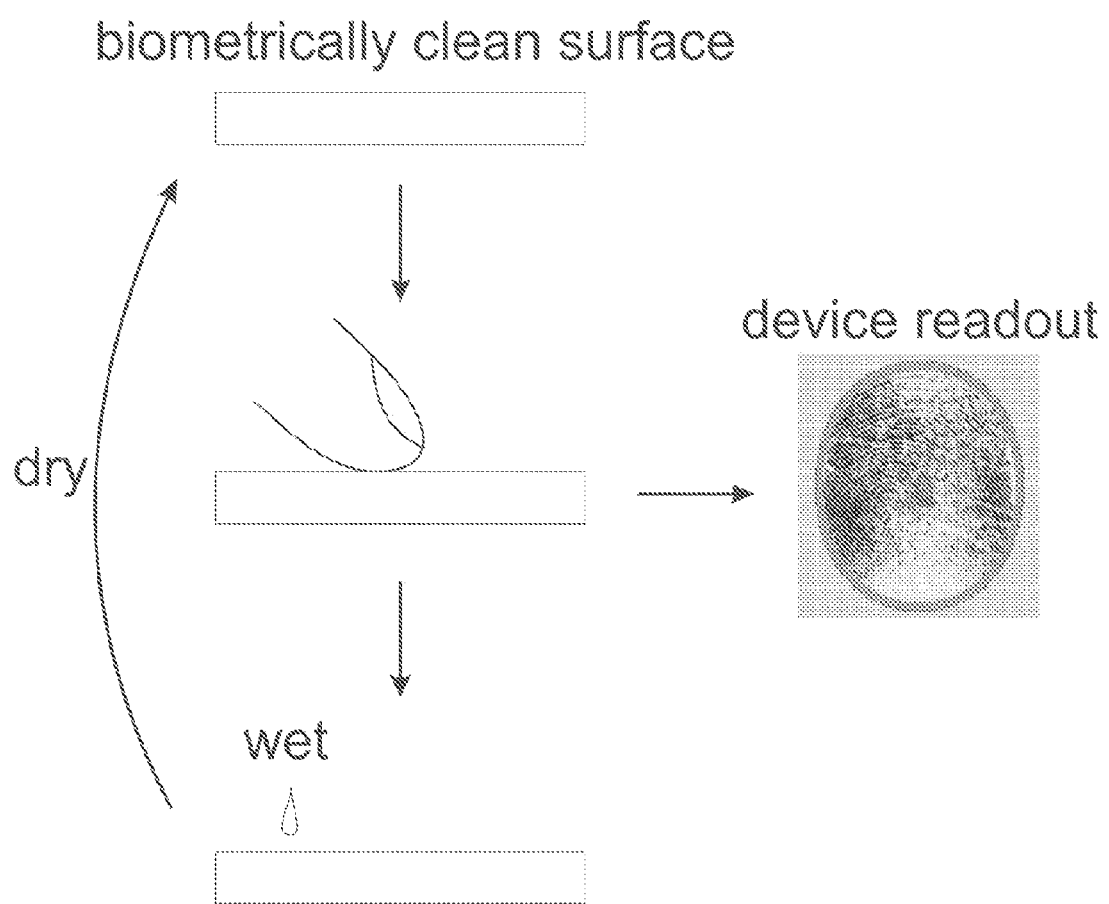
FIG. 5 shows the work flow for obtaining fingerprint (and the like) and its removal from the reconfigurable surface.

For example, as shown in FIG. 5, pressure can be applied onto a biometrically clean surface using a part of a body containing the biometric information (e.g., finger). Thereafter, a scanner can read out the imprinted biometric information. To produce a clean surface, a suitable liquid can be applied to the surface to provide a biometrically clean surface again.

Figure 6:
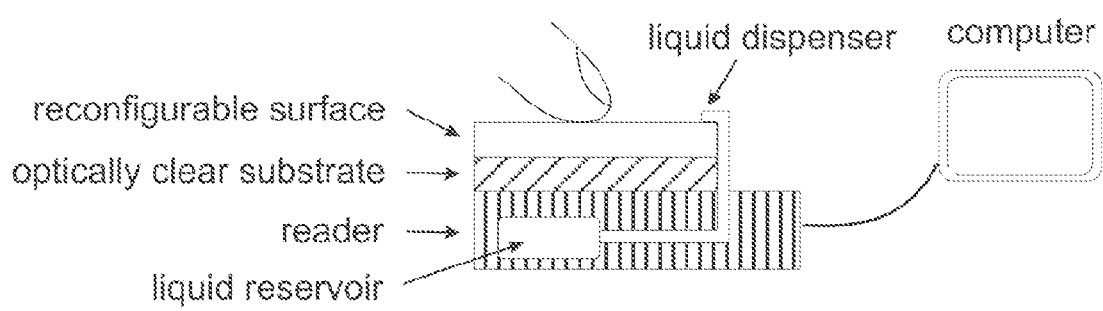
FIG. 6 shows an example of optical fingerprinting device with an integrated reconfigurable surface and automated dispensing fluid system.

The present invention can be used in a full range of biometric machines at government buildings, biometric machines that allow the access to secure documents, security check in on the doors for passing to the secure areas, secure exits, or erasing biometric information on number pads in security safe, car doors, and the like. FIG. 6 shows an exemplary apparatus where the reconfigurable surface is provided over an optically clear substrate. The imprinted biometric information can be read out and/or stored by the reader and computer. The reconfigurable surface can further be connected to a liquid dispenser which can dispense suitable amount of liquid from a liquid reservoir.

The reconfigurable surface and the biometric information apparatus can be manufactured in a number of different ways. As a specific example, the manufacturing process of a sample reconfigurable surface is given as follow. First, a silicon master composed of an array of cylindrical posts (i.e., ~10 μm in post diameter, ~25 μm in pitch, and ~40 μm in height, arranged in square lattice) was first manufactured using standard photolithography and deep reactive ion etching. After the master is made, liquid PDMS mixed with curing agent is poured into the master mold to create a negative replica. After the material is cured, the PDMS negative replica is removed from the master mold and PDMS replica is functionalized with fluorosilane to reduce its adhesion with other foreign materials. To create the positive replica (i.e., the reconfigurable surface), liquid PDMS mixed with the curing agent is then poured into the negative replica. The PDMS positive replica is then removed from the mold after the material is cured. The reconfigurable surface can then be attached onto optically transparent surface such as glass, or other opaque materials. For any physical biometric information that are left on the reconfigurable surfaces, the information can be removed by applying volatile liquids, such as ethanol, onto the surfaces, where the post arrays will reconfigure according to the elastocapillary forces induced by the liquid drying process. The reconfiguration process will erase the physical biometric information accordingly. Other manufacturing processes that can produce raised structures on polymers, such as roll-to-roll printing, are applicable to produce the reconfigurable surfaces.

Upon review of the description and embodiments of the present invention, those skilled in the art will understand that modifications and equivalent substitutions may be performed in carrying out the invention without departing from the essence of the invention, Thus, the invention is not meant to be limiting by the embodiments described explicitly above, and is limited only by the claims which follow.

What is claimed is:

1. A method of removing imprinted biometrics information from surfaces comprising:
   providing a biometric information recording surface comprising a plurality of raised structures,
   reproducing a biometric information on the plurality of raised structures by applying a pressure from a part of a body containing the biometric information to the biometric information recording surface, and
   removing the biometric information by applying a liquid to the plurality of raised structures without a need of applying an external physical contact.

2. The method of claim 1, wherein the plurality of raised structures are clustered.

3. The method of claim 1, wherein the plurality of raised structures comprise a polymer.

4. The method of claim 1, wherein the plurality of raised structures comprise polydimethylsiloxane or polypropylene.

5. The method of claim 1, wherein the biometric information is recorded after reproduction.

6. The method of claim 1, wherein the liquid is a disinfecting liquid.

7. The method of claim 2, wherein said applying a liquid includes wicking the liquid between the plurality of raised structures to form unclustered plurality of raised structures.

8. The method of claim 1, wherein said removing the biometric information includes drying the liquid to form randomly clustered plurality of raised structures.

9. The method of claim 1, wherein biometric information recording surface is provided on an optical reader.

10. The method of claim 9, wherein the optical reader is transparent.

11. The method of claim 1, wherein the biometric information is a fingerprint.

12. The method of claim 11, wherein the biometric information recording surface is a surface of a fingerprint reader in high-traffic security area.

13. The method of claim 1, wherein the biometric information according surface is a surface of a personal number identification pad.

14. The method of claim 1, wherein the biometric information recording surface is a surface of a safe.

15. The method of claim 1, wherein the biometric information recording surface is a surface of a car door lock.

16. The method of claim 1, wherein the biometric information recording surface is a surface of a touch screen device.

17. A biometric information identification device, comprising:
   a biometric information reading optical reader;
   a biometric information recording surface comprising a plurality of raised structures that is capable of reproducing a biometric information on the plurality of raised structures by application of a pressure from a part of a body containing the biometric information to the biometric information recording surface; and
   a liquid that is capable of removing the biometric information by applying the liquid to the plurality of raised structures without a need of applying an external physical contact.

18. The biometric information identification device of claim 17, wherein the plurality of raised structures are clustered.

19. The biometric information identification device of claim 17, wherein the plurality of raised structures comprise a polymer.

20. The biometric information identification device of claim 17, wherein the plurality of raised structures comprise polydimethylsiloxane or polypropylene.

21. The biometric information identification device of claim 17, further comprising a storage device to record the biometric information after reproduction.

22. The biometric information identification device of claim 17, wherein the liquid is a disinfecting liquid.

23. The biometric information identification device of claim 17, wherein the optical reader is transparent.

24. The biometric information identification device of claim 17, wherein the biometric information is a fingerprint.

25. The biometric information identification device of claim 24, wherein the device is a fingerprint reader in a high-traffic security area.

26. The biometric information identification device of claim 17, wherein the device includes a personal number identification pad.

27. The biometric information identification device of claim 17, wherein the device is a safe.

28. The biometric information identification device of claim 17, wherein the device includes a car door lock.

29. The biometric identification device of claim 17, wherein the device is a touch screen device.

* * * * *